US007265101B2

(12) United States Patent
Raskin et al.

(10) Patent No.: US 7,265,101 B2
(45) Date of Patent: Sep. 4, 2007

(54) APPETITE-SUPPRESSING COMPOSITIONS AND METHODS

(75) Inventors: Ilya Raskin, Manalapan, NJ (US); Joseph M. O'Neal, III, Glendora, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/101,357

(22) Filed: Apr. 7, 2005

(65) Prior Publication Data

US 2006/0084638 A1    Apr. 20, 2006

Related U.S. Application Data

(60) Provisional application No. 60/560,144, filed on Apr. 7, 2004.

(51) Int. Cl.
*A61K 31/56* (2006.01)
(52) U.S. Cl. .................................... 514/170
(58) Field of Classification Search ................. 514/170
See application file for complete search history.

(56) References Cited

U.S. PATENT DOCUMENTS

| 6,376,657 B1 | 4/2002 | Van Heerden et al. ............ 536/5 |
| 2003/0152648 A1 | 8/2003 | Corley et al. ................. 424/725 |

FOREIGN PATENT DOCUMENTS

WO    WO 03/041727    *    5/2003

OTHER PUBLICATIONS

Warashina et al., "Steroidal glycosides from the aerial part of *Asclepias incarnata*." Phytochemistry, vol. 53, pp. 485-498, 2000.*
Abe et al., "Pregnane Glycosides from the Roots of *Asclepias tuberosa*," Chem. Pharm. Bull. (Tokyo), 48(7):1017-1022 (2000).
Bent, "The Relative Safety of Ephedra Compared with Other Herbal Products," Annals of Internal Medicine, 138(6):468-471 (2003).
Bonow et al., "Diet, Obesity and Cardiovascular Risk," New England J. Med., 348(21):2057-2058 (2003).
Desai, "Cardiac Glycosides" (2000) Retrieved from the Internet: <URL: http://www.people.vcu.edu/~urdesai/car.htm>.
El Sayed et al., "Pregnane Glycosides From *Stapelia Variegata*," Phytochem., 39(2):395-403 (1995).
Grundy et al., "Definition of Metabolic Syndrome, Report of the National Heart, Lung, and Blood Institute/American Heart Association Conference on Scientific Issues Related to Definition," Circulation, 109(3):433-438 (2004).
Han et al., "Analysis of Obesity and Hyperinsulinemia in the Development of Metabolic Syndrome: San Antonio Heart Study," Obesity Research, 10(9):923-931 (2002).
Marx, "Cellular Warriors at the Battle of the Bulge," Science, 299(5608):846-849 (2003).
"Pleurisy Root-*Asclepias tuberosa*," Physicians' Desk Reference for Herbal Medicines, 2$^{nd}$ ed., pp. 598-599 (2000).

U.S. Department of Agriculture, Natural Resources Conservation Service, Plant Guide, "Butterfly Milkweed *Asclepias tuberosa* L." (Jan. 17, 2001).
U.S. Food and Drug Administration, U.S. Department of Health & Human Services, Press Release, "HHS Acts to Reduce Potential Risks of Dietary Supplements Containing Ephedra" (Feb. 28, 2003).
U.S. Food and Drug Administration, U.S. Department of Health & Human Services, Press Release, "FDA Issues Regulation Prohibiting Sale of Dietary Supplements Containing Ephedrine Alkaloids and Reiterates Its Advice That Consumers Stop Using These Products" (Feb. 6, 2004).
U.S. Food and Drug Administration, U.S. Department of Health & Human Services, Press Release, "HHS Unveils FDA Strategy To Help Reduce Obesity, New 'Calories Count' Approach Builds on HHS' Education, Research Efforts" (Mar. 12, 2004).
Warashina et al., "Steroidal glycosides from the aerial part of *Asclepias incarnata*," Phytochemistry, 53:485-498 (2000).
International Search Report for International (PCT) Patent Application No. PCT/US05/11632, dated Jun. 23, 2005.
Written Opinion of the International Searching Authority for International (PCT) Patent Application No. PCT/US05/11632, dated Jun. 23, 2005.
Dal Piaz et al., "Electrospray Ionization Mass Spectrometry for Identification and Structural Characterization of Pregnane Glycosides," Rapid Comm. Mass. Spec., 19:1041-1052 (Mar. 29, 2005).
MacLean et al., "Increased ATP Content/Production in the Hypothalamus May be a Signal for Energy-Sensing of Satiety: Studies of the Anorectic Mechanism of a Plant Steroidal Glycoside," Science Direct, Brain Research, 1020:1-11 (Jul. 20, 2004).
Nom et al., "Cardiac Glycosides: From Ancient History Through Withiring's Foxglove to Endogeneous Cardia Glycosides," Dan. Medicinhist Arbog.: 119-132 (2004) (Abstract Only).
Schoner, "Ouabain, a New Steroid Hormone of Adrenal Gland and Hypothalamus," Exp;. Clin. Endocrinol Diabetes, 108:449-454 (2000).
Warashina et al., "Steroidal Glycosides From *Cynanchum Caudatum*," Phytochemistry, 39(1):199-204 (1995).
Warashina et al., "Steroidal Glycosides from Roots of *Cynanchum Caudatum*," Phytochemistry, 44(5):917-923 (1997).
Warashina et al., "Steroidal Glycosides from the Aerial Part of *Asclepias incarnata*," Phytochemistry 53:485-498 (2000).
Warashina et al., "Cardenolide and Oxypregnane Glycosides from the Root of *Asclepias incarnata* L.," Chem. Pharm. Bull. 48(4):516-524 (2000).
Warashina et al., "Steroidal Glycosides from the Aerial Part of *Asclepias incarnate* L. II.", Chem. Pharm. Bull., 48(1):99-107 (Jan. 2000). (Abstract Only).

* cited by examiner

Primary Examiner—Barbara P. Badio
(74) Attorney, Agent, or Firm—Marshall, Gerstein & Borun LLP

(57) ABSTRACT

The invention relates to appetite-suppressing compositions obtained from botanical sources. More specifically, the invention relates to appetite-suppressing compositions comprising an extract product of an *Asclepias* plant, methods of making an appetite-suppressing composition, and methods of suppressing an appetite.

10 Claims, 1 Drawing Sheet

APPETITE-SUPPRESSING COMPOSITIONS AND METHODS

CROSS-REFERENCE TO RELATED APPLICATION

The benefit under 35 U.S.C. §119(e) of U.S. provisional patent application Ser. No. 60/560,144 filed Apr. 7, 2004, the entire disclosure of which is incorporated herein by reference, is claimed.

FIELD OF THE INVENTION

The invention relates to appetite-suppressing compositions obtained from botanical sources. More specifically, the invention relates to appetite-suppressing compositions comprising an extract product of an *Asclepias* plant, methods of making an appetite-suppressing composition, and methods of suppressing an individual's appetite.

BACKGROUND OF THE INVENTION

Adult obesity has increased significantly in recent times. For example, recent reports estimate that about 64 percent of Americans are overweight, with more than 30 percent being obese [U.S. Food and Drug Administration, U.S. Department of Health & Human Services, Press Release, Mar. 12, 2004]. Similar reports suggest that poor diet and inactivity are poised to become the leading preventable cause of death among Americans. Thus, obesity and obesity-related disorders such as type II diabetes, hypercholesteremia, and/or metabolic syndrome (also known as syndrome X) are significant problems for modem societies [see also, Han, et al., Obesity Research, 10(9):923-931 (2002); Bonow, New England J. of Med., 348(21):2057-2058 (2003)].

Metabolic syndrome is not a disease state per se, but rather the collective presence in an individual of risk factors such as abdominal obesity, atherogenic dyslipidemia, raised blood pressure, insulin resistance, glucose intolerance, proinflammatory conditions, and prothrombotic conditions [Grundy, et al., Circulation, 109(3):433-8 (2004)]. When one or more (particularly, three or more) of such risk factors is present, the individual has an increased risk for a variety of disease states including diabetes, heart disease, and/or stroke. Individuals having metabolic syndrome are also susceptible to other conditions such as polycystic ovary syndrome, fatty liver, cholesterol gallstones, asthma, sleep disturbances, and some forms of cancer. Most practitioners consider weight reduction to be a primary "therapy" for treating metabolic syndrome. Weight reduction is also considered to be an effective therapy for treating obesity and obesity-related disorders including but not limited to type II diabetes and hypercholesteremia.

Therefore, appetite is one important regulatory pathway that can be targeted to treat obesity and obesity-related disorders [see also, Marx, Science, 299(5608):846-849 (2003)]. Several formulations capable of suppressing appetite are available commercially. Many such known appetite-suppressing formulations contain a mixture of ephedra and caffeine [Bents, Annals of Internal Medicine, 138(6):468-471(2003)]. Although appetite-suppressing formulations containing such mixtures are effective, potentially hazardous side effects are associated with ephedra administration, especially when its use is combined with stimulants such as caffeine [U.S. Food and Drug Administration, U.S. Department of Health & Human Services, Press Release, Feb. 28, 2003]. In view of the aforementioned potentially hazardous side effects, the U.S. Food and Drug Administration banned the sale of dietary supplements containing ephedra [J.S. Food and Drug Administration, U.S. Department of Health & Human Services, Press Release, Feb. 6, 2004]. Thus, safer appetite-suppressing formulations are needed.

U.S. Pat. No. 6,376,657 to Van Heerden, et al. discloses appetite-suppressing compositions containing steroidal compounds. The appetite-suppressing compositions are derived from desert succulent plants of the genera *Trichocaulon* and *Hoodia*, such as *Hoodia gordonii*. Similarly, International Patent Publication No. WO 03/041727 discloses compositions having appetite-suppressing activity derived from desert succulent plants of the genera *Stapelia* and *Orbea*. Such desert succulent plants are native to arid or semi-arid regions, and therefore have adapted to store water in a manner that makes them extremely difficult to propagate and cultivate. For example, such succulent plants typically have reduced leaves with a hard and heavily cutinized outer surface, which minimizes evaporation from the inner plant tissue. More specifically, *Hoodia gordonii* plants take nearly five years to reach maturity, produce only about 0.2 grams of fresh plant material in one month (per plant), and occupy a significant area (over about 500 square centimeters ($cm^2$) per plant). Consequently, *Hoodia gordonii* plants are capable of producing only about 43 grams of fresh plant material per square meter in one year. Thus, the aforementioned plants do not provide a satisfactory source of appetite-suppressing compositions.

The Asclepiadaceae family of plants includes the *Asclepias* genus, as well as diverse genera such as *Trichocaulon, Hoodia, Stapelia*, and *Orbea*. Diversity among plant genera belonging to the same plant family is well-known. Such diversity is often demonstrated by the chemical compounds produced by a plant. For example, the *Solanaceae* plant family contains both *Nicotiana tabacum*(tobacco) and *Lycopersicon esculentum*(tomato), and tobacco plants produce nicotine whereas tomato plants do not.

*Asclepias* is a plant genus belonging to Asclepiadaceae comprising about 75 species of non-succulent "milkweed plants" that may contain poisonous, toxic cardiac glycosides capable of causing death in humans and livestock [U.S. Department of Agriculture, Natural Resources Conservation Service, Plant Guide, Butterfly Milkweed, Jan. 17, 2001]. Such milkweed plants are often grown as food sources for the caterpillars of several species of butterflies. The toxic cardiac glycosides accumulate in the larvae of the butterflies making the butterflies distasteful, thereby providing an effective chemical defense against predators. Compositions derived from *Asclepias* plants such as *Asclepias tuberosa* have been used to treat chest and upper respiratory infections [Physicians' Desk Reference for Herbal-Medicines, $2^{nd}$ ed., 598-599 (2000)]. Although reports suggest that compositions derived from *Asclepias tuberosa* have anti-inflammatory and/or anti-spasmodic activity, their effectiveness in treating the aforementioned respiratory conditions has not been scientifically confirmed [Physicians' Desk Reference website, Pleurisy Root (2004)].

SUMMARY OF THE INVENTION

The invention provides compositions and methods for the suppression of an appetite in an individual. The disclosed methods can be used to treat individuals who are obese and/or are affected by an obesity-related disorder.

One aspect of the invention provides compositions derived from botanical sources. The disclosed botanical compositions possess significant appetite-suppressing activity, and therefore are capable of suppressing appetite in an individual. Advantageously, the disclosed appetite-suppressing compositions are derived from easily cultivatable, non-succulent, plants of the genus *Asclepias*. Accordingly, in one embodiment of this aspect of the invention, the appetite-suppressing compositions include an extract product of an *Asclepias* plant.

Another aspect according to the invention provides methods of making an appetite-suppressing composition comprising providing a plant material of an *Asclepias* plant, contacting the plant material with a solvent, thereby isolating the appetite-suppressing composition. The methods can include a step of disrupting the plant material, for example, by grinding, macerating, or otherwise disrupting the plant material.

In a further aspect, the invention provides methods for suppressing an appetite comprising administering a therapeutically effective amount of a composition containing an extract product of an *Asclepias* plant to an individual. Methods in accordance with the invention have been used to measurably and safely reduce the appetite of an individual.

In yet a further aspect, the invention provides methods for treating obesity or an obesity-related disorder comprising administering a therapeutically effective amount of a composition containing an extract product of an *Asclepias* plant to an individual.

BRIEF DESCRIPTION OF THE DRAWINGS

Objects, features, and advantages of the disclosed appetite-suppressing compositions will become apparent upon reading the following description in conjunction with the sole drawing figure, which illustrates the food intake of animals treated in accordance with the methods and compositions of the invention relative to control animals.

DETAILED DESCRIPTION OF THE INVENTION

Figure 1:
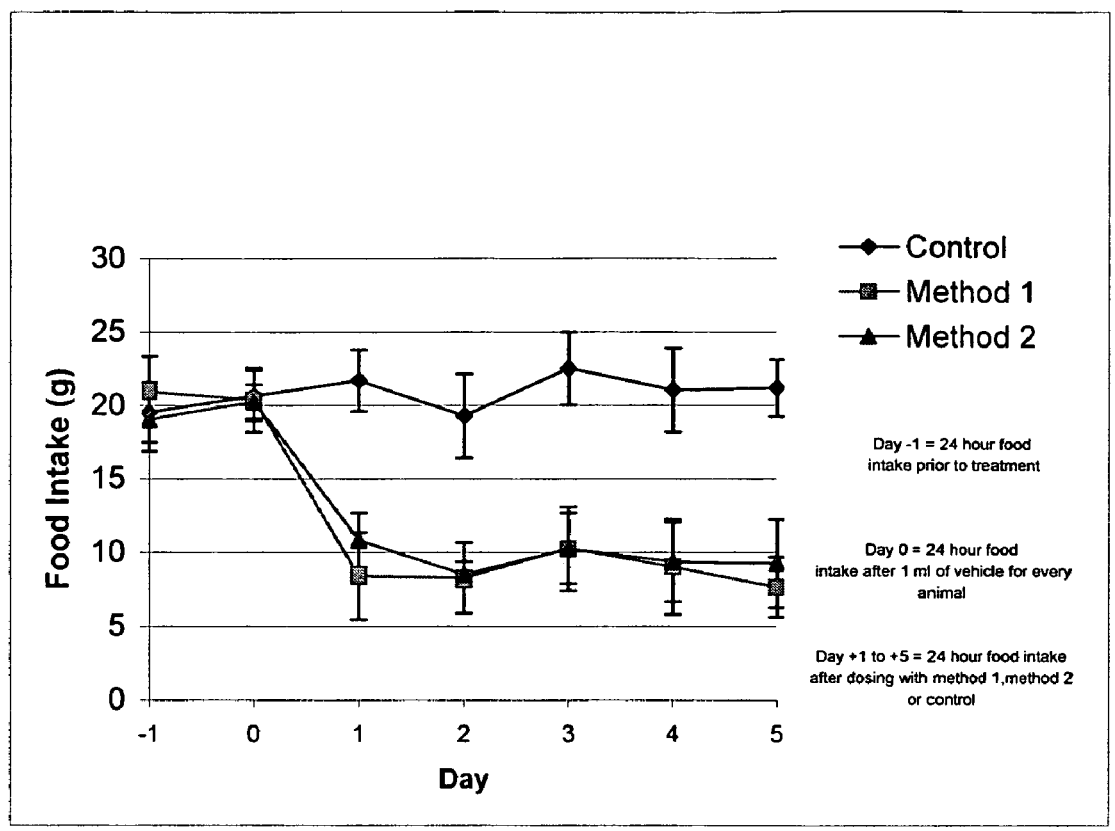

The invention demonstrates that compositions containing an extract product of an *Asclepias* plant possess significant appetite-suppressing activity. Any composition containing an extract product in accordance with the invention, for example, solutions or dried preparations, may be used as a natural alternative to suppress appetite, thereby promoting weight loss and a greater fitness level in an individual.

Accordingly, the disclosed appetite-suppressing compositions can be administered to effectively suppress, inhibit, reduce or otherwise curtail an appetite in an individual. The appetite-suppressing compositions therefore can also be administered to an individual in order to control weight, or to treat obesity or an obesity-related disorder including but not limited to type II diabetes, hypercholesteremia, and metabolic syndrome.

As used herein, "appetite-suppressing" refers to a statistically significant and detectable or measurable reduction in food intake (over a time period of at least about 24 hours) when food is available on an ad libitum, or an equivalent schedule.

As used herein, the term "extract product" refers to any compound, any agent, and/or mixtures thereof, that is obtained, isolated, and/or derived from an extract of a plant material. The term "plant material" refers to any plant material including, but not limited to, leaves, stems, flowers, fruits, seeds, roots, and combinations thereof. In one embodiment, the plant material includes roots only. In another embodiment, the plant material includes the above-ground portions of the plant only.

Typically, the appetite-suppressing compositions contain an extract product of a plant of the genus *Asclepias*. Advantageously, *Asclepias* plants are easy to cultivate and propagate, and provide excellent sources of plant material. Furthermore, *Asclepias* plants possess high contents of appetite-suppressing compounds.

As used herein, the term "easily cultivatable" refers to a plant which is relatively easy to germinate, reasonably resistant to pathogens, responds well to conventional agronomic practices, produces significant amounts of plant material, and is capable of producing multiple crops in a single growing season in the field (or in a year in greenhouse conditions). Plants having such qualities include conventionally known and commercially available vegetable crops. In one aspect according to the invention, easily cultivatable plants are plants which grow from seed to maturity in less than about 1 year, preferably less than about one-half year, and more preferably in about one-quarter year. In another aspect, easily cultivatable plants are plants which are capable of providing greater than about 0.5 grams, preferably more than about 1.0 grams, more preferably more than about 1.5 grams, and even more preferably more than about 2.0 grams of fresh plant material in one month per plant. In yet another aspect, easily cultivatable plants are plants which occupy less than about 25 $cm^2$, preferably less than about 15 $cm^2$, and more preferably less than about 10 $cm^2$ of area per plant. In an additional aspect, easily cultivatable plants are plants which are capable of providing greater than about 500 grams, preferably more than about 1.0 kilogram, more preferably more than about 1.5 kilograms, and even more preferably more than about 2.0 kilograms of fresh plant material per square meter in one year.

*Asclepias* plants in accordance with the invention include, but are not limited to, *A. incarnata, A. curassayica, A. syriaca,* and *A. tuberosa*. Typically, the plants are selected from the group consisting of *A. incarnata, A. curassayica,* and *A. syriaca*.

As demonstrated herein, *Asclepias* plants produce compounds and/or agents having appetite-suppressing activity ("appetite-suppressing compounds"). The appetite-suppressing activity of *Asclepias* plants (and thus, the disclosed appetite-suppressing compositions) is generally attributed to the presence of one or more appetite-suppressing compounds in accordance with the following formulae I, II, and III:

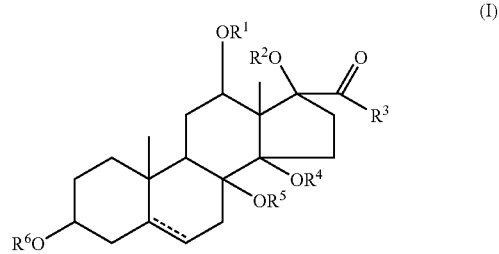

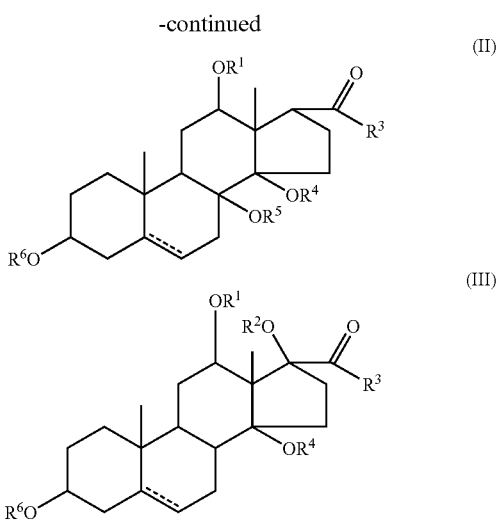

wherein $R^1$ is hydrogen or a $C_1$-$C_{18}$ moiety;
$R^2$ (if present) is hydrogen or a $C_1$-$C_{18}$ moiety;
$R^3$ is a $C_1$-$C_{18}$ moiety;
$R^4$ is hydrogen or a $C_1$-$C_{18}$ moiety;
$R^5$ (if present) is hydrogen or a $C_1$-$C_{18}$ moiety;
$R^6$ is hydrogen, a $C_1$-$C_{18}$ moiety, or a saccharide moiety; and,
the dotted line represents an optional double bond.

As used herein, the term "$C_1$-$C_{18}$ moiety" includes from one to 18 carbon atoms. Typical examples include alkyl, alkylene, heteroalkyl, alkenyl, acyl, and aryl groups as defined herein. Of course, in some embodiments, an individual substituent may be described by more than one of the aforementioned terms.

"Alkyl" as used herein includes straight chain and branched hydrocarbon groups containing up to 18 carbon atoms, for example, one to ten, and one to eight carbon atoms.

"Alkylene" as used herein refers to alkyl groups (as defined) further including one or more substituents.

Additionally, "heteroalkyl" as used herein refers to alkyl groups further containing a heteroatom such as O, P, S, or N.

"Alkenyl" as used herein refers to alkyl groups further containing one or more carbon-carbon double bonds.

"Acyl" as used herein refers to a substituent having the chemical formula A:

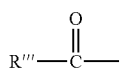

(A)

wherein R''' is a moiety, as defined above, but containing between one and 17 carbon atoms. In preferred embodiments, R''' is selected from the group consisting of aryl and alkylene, particularly alkylenearyl (i.e., an alkylene group having an aryl substituent). Representative acyl groups include formyl, acetyl, propionyl, butyryl, benzoyl, toluoyl, phenylacetyl, tigloyl, and cinnamoyl. In some embodiments, $R^1$ is preferably an acyl group, particularly benzoyl, tigloyl, or cinnamoyl. In some embodiments, the acyl group includes an aryl group containing a heteroatom, as described below.

The term "aryl" is defined herein as a monocyclic or polycyclic aromatic group, preferably a monocyclic or bicyclic aromatic group, e.g., phenyl or naphthyl. An "aryl" group can be unsubstituted or substituted, for example, with one or more, and in particular one to three, halo, alkyl, alkoxy, alkoxyalkyl, haloalkyl, nitro, and/or cyano substituents. The aryl group may also contain one or more heteroatoms such as O, P, S, or N.

The term "saccharide moiety" as used herein refers to a pentose, hexose, heptose, or octose sugar, analog, or derivative thereof, including, but not limited to, deoxy sugars, dideoxy sugars, amino sugars, and sugar acids. The term includes disaccharides, oligosaccharides, and polysaccharides, which are comprised of two or more saccharides that are joined by a glycosidic linkage.

Appetite-suppressing compounds in accordance with formulae I, II, and III include appetite-suppressing compounds in accordance with the following formula IV:

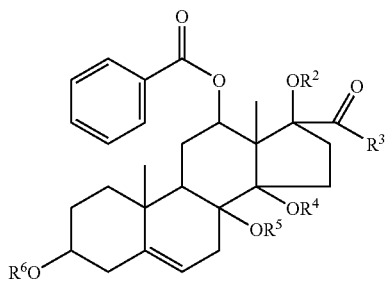

(IV)

wherein $R^2$ (if present) is hydrogen or a $C_1$-$C_{18}$ moiety;
$R^3$ is a $C_1$-$C_{18}$ moiety;
$R^4$ is hydrogen or a $C_1$-$C_{18}$ moiety;
$R^5$ (if present) is hydrogen or a $C_1$-$C_{18}$ moiety; and,
$R^6$ is hydrogen, a $C_1$-$C_{18}$ moiety, or a saccharide moiety.

Appetite-suppressing compounds in accordance with formulae I, II, and III also include appetite-suppressing compounds in accordance with the following formula V:

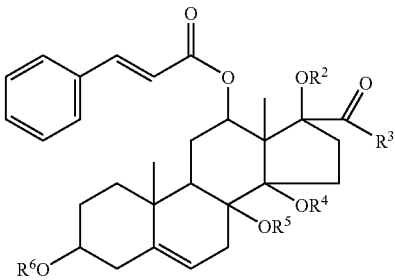

(V)

wherein $R^2$ (if present) is hydrogen or $C_1$-$C_{18}$ moiety;
$R^3$ is $C_1$-$C_{18}$ moiety;
$R^4$ is hydrogen or a $C_1$-$C_{18}$ moiety;
$R^5$ (if present) is hydrogen or a $C_1$-$C_{18}$ moiety; and,
$R^6$ is hydrogen, a $C_1$-$C_{18}$ moiety, or a saccharide moiety.

Although both formulae IV and V are shown as including hydroxyl or alkoxy substituents at both the C17 position (i.e., $OR^2$) and the C8 position (i.e., $OR^5$), formulae IV and V also include appetite-suppressing compounds not containing a hydroxyl or alkoxy substituent at the C17 position (as shown above in Formula II), and appetite-suppressing compounds not containing a hydroxyl or alkoxy substituent at the C8 position (as shown above in Formula III).

Appetite-suppressing compounds in accordance with formulae I, II, III, IV, and/or V are steroidal compounds. In one embodiment, the steroidal compounds are pregnane glycosides (i.e., $R^6$ is a saccharide moiety). In another embodiment, the steroidal compounds are pregnane aglycones (i.e., $R^6$ is hydrogen).

Prior to the invention, no extract possessing significant appetite-suppressing activity and obtained from an easily cultivatable botanical plant source had been made available. Notwithstanding the disclosure of particular compounds having a steroid backbone that were obtained from *A. tuberosa* [Abe, et al., Chem. Pharm. Bull. (Tokyo) 48(7): 1017-1022 (2000)], there has not been any disclosure or suggestion of an *Asclepias* extract product having appetite-suppressing activity. Moreover, formulae I and III (and often formulae IV and V) include an oxygen moiety at C17 (i.e., $OR^2$), which is not present in the steroidal compounds disclosed by Abe and/or U.S. Pat. No. 6,376,657. While International Patent Publication No. WO 03/041727 discloses steroidal compounds having a hydroxyl group at C17, International Patent Publication No. WO 03/041727 does not disclose or suggest the combination of a hydroxyl and a carboxyl group at C17, as shown in the above formulae I and III (and often formulae IV and V).

Similarly, formulae I and II (and often formulae IV and V) include an oxygen moiety at C8 (i.e., $OR^5$) which is not present in the steroidal compounds disclosed by U.S. Pat. No. 6,376,657. Although Abe and International Patent Publication No. WO 03/041727 disclose steroidal compounds having a hydroxyl group at C8, these documents do not disclose or suggest the combination of a hydroxyl and a carboxyl group at C17, as shown in formulae I and III (and often formulae IV and V).

Such differences can result in substantially different activities. For example, cardiac glycosides differing by only one sugar residue have substantially different pharmacokinetics, for example, as measured by a partition coefficient [Desai, "Cardiac Glycosides," Virginia Commonwealth University website, 2000].

The disclosed appetite-suppressing compositions typically contain a mixture of appetite-suppressing compounds in accordance with formulae I, II, III, IV, and/or V. Accordingly, the invention contemplates mixtures, which may exhibit additive, or preferably synergistic, effects.

*Asclepias* plants are grown and harvested using well-known methods. For example, the plants may be grown in an agricultural field. More preferably, the plants are grown in environmentally controlled hydroponic greenhouses using standard hydroponic methods. Hydroponic methods facilitate the reproducible optimization of plant growing conditions, and therefore appetite-suppressing compound content. Hydroponic methods also facilitate harvesting of the plants. Additionally, controlled growth conditions are advantageous in that they facilitate the standardization of any final product.

The conditions under which the plants are grown may also affect the appetite-suppressing compound content. In particular, plants subjected to stress conditions, such as heat stress, dehydration, physical wounding, and/or exposed to chemical elicitors, are expected to have a higher appetite-suppressing compound content than plants not subjected to such conditions. Any conventionally known chemical elicitor can be used during cultivation of the *Asclepias* plants, in accordance with known application schedules.

As previously described, the steroidal compounds are typically isolated by extracting plant material of an *Asclepias* plant. Any plant material, including leaves, stems, flowers, fruits, roots, and combinations thereof, can be extracted. In one embodiment, the above-ground plant parts are extracted. In another embodiment, the plant roots are used.

One exemplary extraction method for obtaining high yields of appetite-suppressing compounds from *Asclepias* plants in accordance with the invention comprises the following steps: (1) providing fresh or fresh-frozen plant material; (2) disrupting the plant material; and (3) extracting the plant material in a solution containing a sufficient amount of solvent; and (4) isolating the extract. The extract may be further processed by: (5) removing solid matter from the extract; (6) removing solvent components; (7) resuspending the resulting residue in an aqueous solution; and (8) after removing any water insoluble material, repeating step (6) to form a more purified form of an extract product. In various embodiments, the plant material can be disrupted by macerating, grinding, or otherwise disrupting the plant material.

In a preferred embodiment, fresh plant tissue is quick-frozen in liquid nitrogen, then ground or otherwise macerated (e.g., using a Polytron or a Waring blender) in solvent. After solids are removed from the extract, e.g., by filtration, centrifugation, or any method known in the art, the appetite-suppressing compound content of the extract can optionally be measured by any known method, including spectrometric methods.

Solvents for use in the extraction methods of the invention include well-known organic solvents such as, but not limited to, water, alcohols, alkanes, halocarbons, ethers, aromatic solvents, ketones, aqueous solvents, esters, and super critical fluids. In one embodiment, ethanol is a preferred alcohol for practice of the invention. A benefit of incorporating an ethanolic solvent in the final extraction step is that an ethanolic solvent is compatible with an ingestible product, and therefore is suitable for incorporation into a pill, capsule, tablet, and other ingestible forms known in the art.

A composition containing an *Asclepias* extract product can be tabletted, encapsulated or otherwise formulated for oral administration (e.g., in a gum or candy). The compositions may be provided as pharmaceutical compositions (e.g., an ethical drug), nutraceutical compositions (e.g., a dietary supplement), or as a food or beverage additive, as defined by the U.S. Food and Drug Administration.

The compositions typically include one or more suitable diluents, fillers, salts, disintegrants, binders, lubricants, glidants, wetting agents, controlled release matrices, colorants, flavoring, carriers, excipients, buffers, stabilizers, solubilizers, commercial adjuvants, and/or other additives known in the art.

Any pharmaceutically acceptable (i.e., sterile and acceptably non-toxic as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Such compositions may influence the physical state, stability, rate of in vivo release, and rate of in vivo clearance of the present appetite-suppressing compounds.

Pharmaceutically acceptable fillers can include, for example, lactose, microcrystalline cellulose, dicalcium phosphate, tricalcium phosphate, calcium sulfate, dextrose, mannitol, and/or sucrose. Salts, including calcium triphosphate, magnesium carbonate, and sodium chloride, may also be used as fillers in the pharmaceutical compositions.

Binders may be used to hold the composition containing the extract product together to form a hard tablet. Exemplary binders include materials from natural products such as acacia, tragacanth, starch and gelatin. Other suitable binders include methyl cellulose (MC), ethyl cellulose (EC) and carboxymethyl cellulose (CMC).

As set forth in Examples 3 and 4, methods in accordance with the invention have been used to measurably and safely reduce appetite and result in lower food consumption. The methods for suppressing an appetite include administering to an individual a therapeutically effective amount of a composition containing an extract product of a plant material of an *Asclepias* plant.

In another embodiment, the invention provides methods for treating obesity or an obesity-related disorder comprising administering a therapeutically effective amount of a composition containing an extract product of a plant material of an *Asclepias* plant to an individual. Obesity and obesity-related disorders including but not limited to type II diabetes, hypercholesteremia, and metabolic syndrome are contemplated for treatment. In one aspect, the individual has at least one risk factor selected from the group consisting of abdominal obesity, atherogenic dyslipidemia, raised blood pressure, insulin resistance, glucose intolerance, proinflammatory conditions, and prothrombotic conditions.

As used herein, "abdominal obesity" refers to an individual having an increased waist circumference, and typically is present in a human male having a waist greater than about 40 inches and in a human female having a waist greater than about 35 inches. In an alternative aspect, abdominal obesity refers to individuals with body mass indices (i.e., [(individual's weight in pounds)/(individual's height in inches)$^2$ times 703]) exceeding about 25, more typically more than about 30.

"Atherogenic dyslipidemia" refers to an elevated triglyceride concentration (serum concentration $\geq$ 150 mg/dL) and/or a depressed high-density lipoprotein cholesterol concentration (serum concentration $\leq$ 40 mg/dL for a male or $\leq$ 50 mg/dL for a female) in an individual.

"Raised blood pressure" refers to an individual having a systolic pressure exceeding about 130 mm Hg and/or a diastolic pressure exceeding about 85 mm Hg.

"Insulin resistance" refers to a condition wherein a given concentration of insulin produces a less-than-expected biological effect. Insulin resistance generally refers to individuals requiring 200 or more units of insulin per day to attain glycemic control and prevent ketosis.

"Glucose intolerance" refers to an individual having a serum glucose concentration exceeding about 100 mg/dL.

As used herein, "proinflammatory conditions" refer to elevated concentrations of C-reactive protein, and "prothrombotic conditions" refer to increased plasminogen activator inhibitor (PAI)-1 and fibrinogen levels relative to healthy individuals, as is generally known.

Thus, in one embodiment, the term "therapeutically effective amount" refers to an amount of a composition containing an *Asclepias* extract product that is sufficient to reduce, decrease, and/or inhibit appetite in an individual. In an alternative embodiment, the term "therapeutically effective amount" refers to an amount of composition containing an *Asclepias* extract product that is sufficient to alleviate, ameliorate, prevent, and/or clear the symptoms and/or the pathology of a condition associated with obesity or an obesity-related disorder such as type II diabetes, hypercholesteremia, and/or metabolic syndrome.

The methods in accordance with the invention contemplate administration of an *Asclepias* extract product containing composition whether or not symptoms are manifest, i.e., prophylactic administration is contemplated. Because preferred dosages of weight loss therapeutics such as sibutramine and orlistat are known in the art for a variety of therapeutic and prophylactic purposes, appropriate dosages of the appetite-suppressing compositions in accordance with the invention may be easily determined by standard methods.

The methods can be used alone or in conjunction with other therapies including, for example, administration of other therapeutic agents (including other appetite-suppressing compositions or formulations), and/or exercise programs.

It will be appreciated that the treatment methods of the invention are useful in the fields of human medicine and veterinary medicine. Thus, the subject or individual to be treated may be a mammal, preferably human, or other animals. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In the methods according to the invention, the appetite-suppressing compositions may be administered by any known route of administration. For example, a composition containing an extract product of an *Asclepias* plant can be formulated for injection, or for oral, nasal, transdermal or other forms of administration. Typically, the appetite-suppressing compositions are formulated for topical, oral, or nasal administration, particularly for oral administration. In some embodiments, the appetite-suppressing compositions are prepared using a non-toxic alcohol or an aqueous solution.

A typical treatment course may comprise multiple doses of a composition containing an amount of an *Asclepias* extract product effective to suppress an appetite in an individual on a daily basis for significant periods of time, for example, three doses per day over three months. In one embodiment, a presently preferred dose amount is one dose per day. The compositions may be administered to an individual at any time. Typically, the compositions are administered at least one hour before consumption of food is anticipated.

Of course, these are only exemplary treatment schedules, and other schedules are contemplated. In each case, the suitability of such schedules and the aforementioned modes of administration are determined by those of skill in the art, using routine procedures. For example, those of skill in the art will be able to take the information disclosed in this specification and optimize treatment regimes for human subjects based on clinical trials performed in accordance with the specification.

The following Examples are provided to describe the invention in greater detail, and are intended to illustrate, not to limit, the appended claims.

EXAMPLE 1

Methods of Extracting an Asclepias Plant Material

Two exemplary methods for extracting an *Asclepias* plant material, thereby providing a composition containing an extract product and having appetite-suppressing activity, are described. The first extraction method provides extract products rich in pregnane glycosides. The second extraction method provides extract products rich in pregnane aglycones, possibly because of the hydrolysis of the saccharide moieties represented, for example, by $R^6$ in formulae I, II, III, IV, and V above. Additionally, extracts obtained using both protocols were analyzed by liquid chromatography mass spectroscopy ("LC-MS") to provide additional information regarding the compositions containing extract products.

In the first method, fresh hydroponically grown root material was frozen at −20° C. The frozen root material was lyophilized for 48 hours until dry. The dried root material was ground by mortar and pestle. Ten grams of root material were then extracted for 24 hours in 0.5 liters of a mixture of methylene chloride and methanol (about 1 part methylene chloride to about 1 part methanol by volume). The solid plant material was removed by filtration through Miracloth™ filter paper and the remaining solvent was removed under reduced pressure using a rotary evaporation device having a 38° C. water bath. The dried, crude extract was dissolved in 250 milliliters (ml) of ultrapure water and partitioned against 0.5 liters of methylene chloride. The methylene chloride fraction was saved and the solvent removed by rotary evaporation. The water fraction was discarded. The dry extract was dissolved in 150 ml of methanol and partitioned twice against 300 ml of hexanes. The solvent of the methanol fraction was removed by rotary evaporation. The resulting "active" fraction was dissolved in 300 ml of water, frozen at −20° C., and lyophilized to provide an extract product in the form of a dry powder.

In the second method, fresh hydroponically grown root material was frozen at −20° C. The frozen root material was lyophilized for 48 hours until dry. The dried root material was ground by mortar and pestle. Ten grams of dry root material was then extracted for 24 hours in 0.5 liters of 100% ethanol. The solid plant material was removed by filtration through Miracloth™ filter paper and the remaining solvent was removed from the extract using a rotary evaporation device having a 38° C. water bath. The dried extract was dissolved in 0.5 liters of 0.5 N HCl for 24 hours. The solid plant material was removed by filtration through the filter paper. The pH of the solution was adjusted to about 9.5 with 20-22% (approximately 45 ml) of ammonium hydroxide to provide a basic solution. 1.0 liter of chloroform was added to the basic solution. The chloroform fraction was isolated and the chloroform was removed using a rotary evaporation device. The dried extract product was stored at −20° C.

Approximately two weight percent of an appetite-suppressing extract product is obtained per kilogram of fresh plant material (i.e., 20 grams of an extract product per kilogram of fresh *Asclepias* plant material). Further purification (e.g., by chromatographic methods) of the extract product could increase the efficacy of the appetite-suppressing extract product and/or reduce the dose needed to effectively suppress appetite in an individual.

EXAMPLE 2

Isolation and Identification of Pregnane Structures

Compositions containing extract products in accordance with the invention were analyzed to determine if they contained pregnane steroidal compounds. LC-MS analysis confirmed that pregnane structures in accordance with formulae I, II, and/or III are present in extract products of *A. incarnata* and *A. curassayica* prepared in accordance with the exemplary extraction methods of Example 1.

This Example further demonstrates that compositions in accordance with the invention typically contain a mixture of pregnane glycosides and aglycones. For example, HPLC fractionation was performed on an extract product of *A. curassayica* that was prepared in accordance with the second extraction method of Example 1. Subsequent analysis of fractions corresponding to several of the resulting peaks led to the structural identification of two pregnane backbones. MS fragmentation patterns and/or proton and carbon thirteen NMR experiments were used to identify the specific pregnane backbones.

EXAMPLE 3

Administration of Appetite-Suppressing Compositions to Rats and Measured Effects on Rat-Feeding Behavior Three studies were performed to evaluate the appetite-suppressing activity of compositions containing extract products in accordance with the invention on animal subjects. Animal studies were performed using extract products of *A. incarnata* that were prepared in accordance with the first extraction method of Example 1.

Study 1:

Nine Sprague-Dawley rats weighing approximately 400 grams each were placed on a powder diet (certified rodent diet meal #5002M, PMI Nutrition Int., Richmond, Ind.) and separated into three groups of three animals (a control group, a group that received a comparison appetite-suppressing composition (i.e., a *Hoodia gordonii* extract), and a group that received an extract product in accordance with the invention). The feed was supplied via specially designed feeding containers (series 148 feeder, Unifab Corp., Kalamazoo, Mich.) that minimize food spillage.

Twenty-four hours prior to treatment, food container weights and body weights for all nine rats were measured and recorded. The containers were again weighed immediately before treatment, giving an average animal food consumption for the 24 hour period before dosing. The three groups each were given intraperitoneal (IP) injections of either (1) a control vehicle, (2) an extract of *Hoodia gordonii*, or (3) an extract product of the first method of Example 1 at the beginning of day 0 (3 PM).

The control group received IP injection of a solution containing a carrier only, specifically 2 weight percent ("wt. %") carboxymethylcellulose (CMC). No appetite-suppressing compositions were administered to the control group. The second group received IP injection of 2 ml of a solution containing 90 mg of a *Hoodia gordonii* extract and 2.0 wt. % CMC. The third group received IP injection of 2 ml of a solution containing 120 mg of an *Asclepias* extract product and CMC, wherein the *Asclepias* extract was prepared in accordance with the first extraction method of Example 1.

The *Hoodia gordonii* extract was prepared by extracting *Hoodia gordonii* shoots for 24 hours in 0.5 liters of a one-to-one mixture of methylene chloride and methanol. The solvent was removed to provide a dried, crude extract, which was then dissolved in 250 milliliters (ml) of ultrapure water and partitioned against 0.5 liters of methylene chloride. The methylene chloride fraction was saved and the solvent was removed to provide a dried extract. The dried extract was dissolved in 150 ml of methanol and partitioned twice against 300 ml of hexanes. The methanol fraction was saved and the solvent was removed. The resulting dried extract was dissolved in 300 ml of water, frozen at −20° C. and lyophilized to provide a dry powder.

The weights of the various food containers were measured approximately 16 hours and 24 hours after dosing. Body weights were also measured at 3:35 pm of day 1 (approximately 24.5 hours after administration). This 24-hour feeding study was performed at Product Safety Labs, Dayton, N.J.

The data set forth in Table I demonstrate the appetite-suppressing activity of the compositions in accordance with the invention. For example, whereas the appetites of the rats in the control group were decreased by approximately 17.5 percent, the appetites of the rats in the group receiving a solution containing a *Hoodia gordonii* extract were decreased by approximately 87.2 percent, and the appetites of the rats in the group receiving a solution containing an *Asclepias* extract product were decreased by approximately 93.0 percent. Accordingly, this Example demonstrates that the disclosed appetite-suppressing compositions possess significant appetite-suppressing activity.

TABLE I

| Animal Group | Average feed consumed (grams) | standard deviation (grams) |
|---|---|---|
| All Animals (before treatment) | 23.44 | 2.40 |
| Control Group | 19.33 | 0.58 |
| Group 2 (*Hoodia gordonii*) | 3.00 | 2.00 |
| Group 3 (*Asclepias*) | 1.67 | 2.08 |

Study 2:

Nine male Wistar rats, each animal weighing approximately 150 grams, were divided into three groups of 3 animals (a control group and two groups that received different doses of an extract product in accordance with the invention). The rats were placed on a powder diet (certified rodent diet meal #5002M, PMI Nutrition Int., Richmond, Ind.) at least two weeks prior to dosing.

An extract product of *A. incarnata* (obtained using the first extraction method of Example 1) was suspended in distilled water. Approximately 1.25 ml of this solution was administered to the animals by oral gavage. The control group received 1.25 ml of water only, i.e., no appetite-suppressing compositions were administered to the control group. The second group received 1.25 ml of a solution containing 40 mg of an *Asclepias* extract product in water, wherein the *Asclepias* extract product was prepared in accordance with the first extraction method of Example 1. The third group received 1.25 ml of a solution containing 60 mg of an *Asclepias* extract product in water, wherein the extract product was prepared analogously to the *Asclepias* extract.

Food consumption was measured 24 hours after dosing. This study was performed in the Small Animal Research Facilities of Cook College, Rutgers University.

The data set forth in Table II further demonstrate the appetite-suppressing activity of the compositions in accordance with the invention. For example, the appetites of the rats in the group receiving a solution containing 40 mg of an *Asclepias* extract product were decreased by approximately 21.4 percent relative to the control group. Additionally, the appetites of the rats in the group receiving a solution containing 60 mg of an *Asclepias* extract product were decreased by approximately 45.1 percent relative to the control group. Therefore, this Example demonstrates that the disclosed appetite-suppressing compositions possess significant appetite-suppressing activity.

TABLE II

| Animal Group | Average feed consumed (grams) | standard deviation (grams) |
|---|---|---|
| All Animals (before treatment) | 28.78 | 4.48 |
| Control Group (24 hours after treatment) | 20.2 | 4.21 |
| Group 2 (*Asclepias*, 24 hours after treatment, 40 mg/animal) | 15.9 | 0.06 |
| Group 3 (*Asclepias*, 24 hours after treatment, 60 mg/animal) | 11.1 | 5.58 |

Study 3:

Ten male Wistar rats, each animal weighing approximately 375 grams, were divided into two groups of five animals each (a control group and a group that received an extract product in accordance with the invention). The rats were placed on a powder diet (certified rodent diet meal #5002M, PMI Nutrition Int., Richmond, Ind.) at least two weeks prior to dosing.

An extract product of *A. incarnata* that was obtained using the first extraction method of Example 1 was suspended in a solution comprising distilled water and 2.0 weight percent (wt. %) CMC. The control group received 1.25 ml of CMC solution only, i.e., no appetite-suppressing compositions were administered to the control group. The second group received 1.25 ml of a solution containing 170 mg of an *Asclepias* extract product, wherein the *Asclepias* extract product was prepared in accordance with the first extraction method of Example 1.

The test material and control were delivered by oral gavage and food consumption was monitored every 24 hours for 48 hours. Food consumption for all animals was also monitored for 24 hours prior to dosing. This study was performed in the Small Animal Research Facilities of Cook College, Rutgers University.

The data set forth in Table III further demonstrate the appetite-suppressing activity of the compositions in accordance with the invention. For example, whereas the appetites of the rats in the control group were increased after 24 hours by approximately 7.8 percent, the appetites of the rats in the group receiving a solution containing an *Asclepias* extract product were decreased by approximately 23.7 percent. Further, whereas the appetites of the rats in the control group were decreased after 48 hours by approximately 13.1 percent, the appetites of the rats in the group receiving a solution containing an *Asclepias* extract product were decreased by approximately 43.3 percent. Therefore, this Example demonstrates that the disclosed appetite-suppressing compositions possess significant appetite-suppressing activity.

Finally, an outlying animal, which had a disproportionately reduced appetite when compared with the other animals in its group, was removed from the second group, as reported herein. Thus, the number of animals in this group was four.

TABLE III

| Animal Group | Average feed consumed (grams) | standard deviation |
|---|---|---|
| All Animals (before treatment) | 23.08 | 4.10 |
| Control Group (24 hours after treatment) | 24.88 | 6.25 |
| Control Group (48 hours after treatment) | 20.05 | 1.05 |
| Group 2 (*Asclepias*, 24 hours after treatment) | 17.60 | 2.65 |
| Group 2 (*Asclepias*, 48 hours after treatment) | 13.08 | 2.78 |

Study 4:

Fifteen male Wistar rats, each animal weighing approximately 270 grams, were divided into three groups of five animals each (a control group, a group that received a comparison appetite-suppressing composition (i.e., containing a *Hoodia gordonii* extract), and a group that received an extract product in accordance with the invention). The rats were placed on a powder diet (certified rodent diet meal #5002M, PMI Nutrition Int., Richmond, Ind.) at least two weeks prior to dosing.

The control group received 0.5 ml of a solution containing 2 wt. % CMC solution only, i.e., no appetite-suppressing compositions were administered to the control group. The second group received 0.5 ml of a solution containing 2 wt. % CMC and 30 mg ephedra free Trim Spa™ (Trim Spa™ tablets were ground for this purpose). The third group received 0.5 ml of a solution containing 30 mg of an *A. incarnate* extract product (obtained using the first extraction method of Example 1) and 2 wt. % CMC. The test material and control were delivered by oral gavage.

TrimSpa™ is a commercially available nutraceutical weight loss product that lists *Hoodia gordonii* as an ingredient. The tablets contain about 5 weight percent of *Hoodia gordonii* plant material (whole plant less roots).

The data set forth in Table IV also demonstrate the appetite-suppressing activity of the compositions in accordance with the invention. For example, the appetites of the rats in the group receiving an *Asclepias* extract product were decreased by approximately 40.3 percent relative to the control group after five days of treatment. Further, this Example demonstrates that the disclosed appetite-suppressing compositions possess significant appetite-suppressing activity when compared with a commercially available composition containing *Hoodia gordonii* plant material.

TABLE IV

| Animal Group | Average feed consumed (grams) | standard deviation |
|---|---|---|
| All Animals (before treatment) | 24.10 | 2.61 |
| Control Group (24 hours after treatment) | 24.62 | 1.51 |
| Control Group (48 hours after treatment) | 24.46 | 1.49 |
| Control Group (72 hours after treatment) | 24.26 | 1.68 |
| Control Group (96 hours after treatment) | 25.06 | 2.09 |
| Control Group (120 hours after treatment) | 23.92 | 2.65 |
| Group 2 (TrimSpa™, 24 hours after treatment) | 21.14 | 2.13 |
| Group 2 (TrimSpa™, 48 hours after treatment) | 23.24 | 2.06 |
| Group 2 (TrimSpa™, 72 hours after treatment) | 21.50 | 1.58 |
| Group 2 (TrimSpa™, 96 hours after treatment) | 23.00 | 3.35 |
| Group 2 (TrimSpa™, 120 hours after treatment) | 20.80 | 1.76 |
| Group 3 (*Asclepias*, 24 hours after treatment) | 20.40 | 3.07 |
| Group 3 (*Asclepias*, 48 hours after treatment) | 18.28 | 4.49 |
| Group 3 (*Asclepias*, 72 hours after treatment) | 14.78 | 4.64 |
| Group 3 (*Asclepias*, 96 hours after treatment) | 16.64 | 5.33 |
| Group 3 (*Asclepias*, 120 hours after treatment) | 14.26 | 2.98 |

EXAMPLE 4

Administration of Appetite-Suppressing Compositions to Rats and Measured Effects on Rat-Feeding Behavior Studies were also performed to determine whether an additional alternative extraction method provided extract product compositions possessing appetite-suppressing activity. The animal studies were performed using extract products of *A. incarnata* prepared according to the following two methods.

In both of the following extraction methods, root material obtained from *A. incarnata* plants that were grown using hydroponic greenhouses was first harvested, then stored frozen for nearly 60 days, and subsequently lyophilized until dry. The lyophilized root material was stored for nearly 180 days before being extracted according to one of the following two extraction methods:

In the first extraction method, 200 grams of the above lyophilized root material were extracted for 24 hours in 2.0 liters of a mixture of methylene chloride and methanol (about 1 part methylene chloride to about 1 part methanol by volume). The extract was filtered using filter paper and the remaining solvent was removed under reduced pressure using a rotary evaporation device. The dried, crude extract was dissolved in 1.5 liters of distilled water and partitioned against 1.5 liters of methylene chloride. The methylene chloride fraction was saved and the solvent removed by rotary evaporation. The water fraction was discarded. The dry extract product was dissolved in 1 liter of methanol and partitioned against 1 liter of hexanes. The solvent of the methanol fraction was removed by rotary evaporation. The hexanes fraction was discarded. The resulting "active" methanol fraction provided 3.8 grams of an extract product in accordance with the invention.

In the second extraction method, 200 grams of the above lyophilized root material were extracted for 24 hours in 2.0 liters of 95% ethanol. The extract was filtered using filter paper and the remaining solvent was removed under reduced pressure using a rotary evaporation device. The dried, crude extract was dissolved in 1.5 liters of distilled water and partitioned against 1.5 liters of ethyl acetate. The ethyl acetate fraction was saved and the solvent removed by rotary evaporation. The water fraction was discarded. The resulting "active" ethyl acetate fraction provided 4.0 grams of an extract product in accordance with the invention. Thus, the second extraction method resulted in greater extract product yield, and was faster and simpler relative to the first method (as it only used a single partitioning step).

Fifteen male Wistar rats, each animal weighing between approximately 176 grams and approximately 200 grams, were randomly divided into three groups of five animals each (a control group, a group that received an extract product obtained using the first extraction method of this Example, and a group that received an extract product obtained using the second extraction method of this Example). The rats were individually caged, and food (AIN-76A pellets, Dyets Inc., Bethlehem, Pa.) and water were available on an ad libitum basis.

Twenty-four hours prior to treatment, food container weights for all fifteen rats were measured and recorded (thus, food intake was measured). All 15 animals then received 1 ml of a solution containing 2.0 wt. % CMC by oral gavage.

The food containers were again weighed immediately before treatment, giving a second average animal food consumption before dosing.

For the following five days, the control group then received a solution containing a carrier only, specifically 2 weight percent ("wt. %") carboxymethylcellulose (CMC) by oral gavage. No appetite-suppressing compositions were administered to the control group.

For the following five days, the second group received 1 ml of a solution containing 30 mg of an *Asclepias* extract product and 2.0 wt. % CMC by oral gavage, wherein the extract product was obtained using the first extraction method of this Example.

Similarly, the third group also received 1 ml of a solution containing 30 mg of an *Asclepias* extract product and 2.0 wt. % CMC by oral gavage for the following five days, but the extract product was obtained using the second extraction method of this Example.

The weights of the various food containers were measured approximately 24 hours after each dosing. The data set forth in FIG. 1 further demonstrate the appetite-suppressing activity of the compositions in accordance with the invention. For example, the appetites of the rats in the groups receiving a solution containing an *Asclepias* extract product were decreased by approximately 50 percent relative to the control group. Therefore, this Example also demonstrates that the disclosed appetite-suppressing compositions possess significant appetite-suppressing activity.

Furthermore, this Example demonstrates that *Asclepias* plants grown using large-scale cultivation practices possess significant appetite-suppressing activity, that the active constituents of an *Asclepias* extract product are stable at room temperature, and that the simpler extraction method described in this Example provides effective appetite-suppressing compositions.

The invention is not limited to the embodiments described and exemplified above, but rather is capable of variation and modification without departure from the scope of the appended claims.

The invention claimed is:

1. A method of suppressing appetite, comprising:
administering a therapeutically effective amount of a composition containing an extract product of a plant material of an *Asciepias* plant to an individual desirous of a suppressed appetite.

2. The method of claim 1, wherein the plant material is selected from the group consisting of leaves, stems, flowers, fruits and roots.

3. The method of claim 1, wherein the plant is selected from the group consisting of *A. incarnata, A. curassavica, A. syriaca* and *A. tuberosa*.

4. The method of claim 1, wherein the extract product comprises compounds in accordance with the following formula (I):

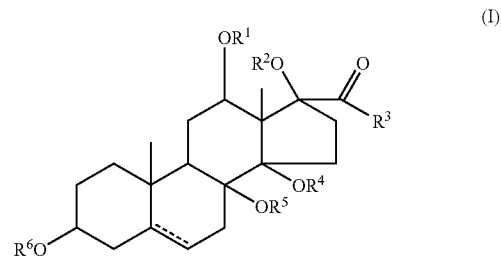

wherein $R^1$ is hydrogen or a $C_1$-$C_{18}$ moiety;
$R^2$ is hydrogen or a $C_1$-$C_{18}$ moiety;
$R^3$ is a $C_1$-$C_{18}$ moiety;
$R^4$ is hydrogen or a $C_1$-$C_{18}$ moiety;
$R^5$ is hydrogen or a $C_1$-$C_{18}$ moiety;
$R^6$ hydrogen, a $C_1$-$C_{18}$ moiety, or a saccharide moiety; and,
the dotted line represents an optional double bond.

5. The method of claim 1, wherein the extract product comprises compounds in accordance with the following formula (II):

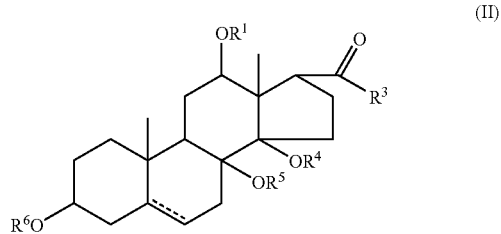

wherein $R^1$ is hydrogen or a $C_1$-$C_{18}$ moiety;
$R^3$ is a $C_1$-$C^{18}$ moiety;
$R^4$ hydrogen or a $C_1$-$C_{18}$ moiety;
$R^5$ hydrogen or a $C_1$-$C_{18}$ moiety;
$R^6$ hydrogen, a $C_1$-$C_{18}$ moiety, or a saccharide moiety; and,
the dotted line represents an optional double bond.

6. The method of claim 1, wherein the extract product comprises compounds in accordance with the following formula (III):

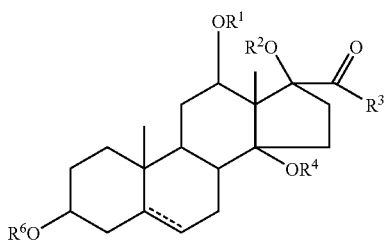

(III)

wherein $R^1$ is hydrogen or a $C_1$-$C_{18}$ moiety;
$R^2$ is hydrogen or a $C_1$-$C_{18}$ moiety;
$R^3$ is a $C_1$-$C_{18}$ moiety;
$R^4$ is hydrogen or a $C_1$-$C_{18}$ moiety;
$R^6$ is hydrogen, a $C_1$-$C_{18}$ moiety, or a saccharide moiety; and,
the dotted line represents an optional double bond.

7. The method of claim 1, wherein the individual is a mammal.

8. The method of claim 1, wherein the individual is obese or has an obesity-related disorder.

9. The method of claim 8, wherein the obesity-related disorder is selected from the group consisting of type II diabetes, hypercholesteremia and metabolic syndrome.

10. The method of claim 9, wherein the individual has at least one risk factor selected from the group consisting of abdominal obesity, atherogenic dyslipidemia, raised blood pressure, insulin resistance, glucose intolerance, proinflammatory conditions and prothrombotic conditions.

* * * * *

UNITED STATES PATENT AND TRADEMARK OFFICE
CERTIFICATE OF CORRECTION

PATENT NO. : 7,265,101 B2
APPLICATION NO. : 11/101357
DATED : September 4, 2007
INVENTOR(S) : Ilya Raskin et al.

It is certified that error appears in the above-identified patent and that said Letters Patent is hereby corrected as shown below:

At Column 18, line 58, "$C_1$-$C^{18}$" should be -- $C_1$-$C_{18}$ --.

Signed and Sealed this

Sixth Day of May, 2008

JON W. DUDAS
*Director of the United States Patent and Trademark Office*